United States Patent
Arcand et al.

(10) Patent No.: US 9,452,040 B2
(45) Date of Patent: Sep. 27, 2016

(54) EMBOLIC PROTECTION DEVICES WITH AN IMPROVED FILTER MEMBRANE

(75) Inventors: Ben Arcand, Minneapolis, MN (US); Greg Dallman, Princeton, MN (US); Jim Anderson, Fridley, MN (US); Erin Guest, Minneapolis, MN (US); Kyle Hendrikson, Litchfield, MN (US); Al Utke, Andover, MN (US)

(73) Assignee: BOSTON SCIENTIFIC SCIMED INC., Maple Grove, MN (US)

( * ) Notice: Subject to any disclaimer, the term of this patent is extended or adjusted under 35 U.S.C. 154(b) by 1854 days.

(21) Appl. No.: 12/548,558

(22) Filed: Aug. 27, 2009

(65) Prior Publication Data

US 2011/0054514 A1  Mar. 3, 2011

(51) Int. Cl.
*A61M 29/00* (2006.01)
*A61F 2/01* (2006.01)

(52) U.S. Cl.
CPC .......... *A61F 2/013* (2013.01); *A61F 2002/018* (2013.01); *A61F 2230/0006* (2013.01); *A61F 2230/008* (2013.01); *A61F 2230/0067* (2013.01); *Y10T 29/49826* (2015.01)

(58) Field of Classification Search
USPC ....................................................... 606/200
See application file for complete search history.

(56) References Cited

U.S. PATENT DOCUMENTS

| | | | |
|---|---|---|---|
| 6,695,865 B2 * | 2/2004 | Boyle et al. | 606/200 |
| 6,890,341 B2 * | 5/2005 | Dieck et al. | 606/200 |
| 7,163,549 B2 | 1/2007 | Crank et al. | |
| 7,174,636 B2 | 2/2007 | Lowe | |
| 7,323,001 B2 | 1/2008 | Clubb et al. | |
| 7,473,265 B2 | 1/2009 | Linder et al. | |
| 7,481,823 B2 | 1/2009 | Broome et al. | |
| 2003/0124279 A1 * | 7/2003 | Sridharan et al. | 428/35.7 |
| 2004/0138694 A1 | 7/2004 | Tran et al. | |
| 2004/0153117 A1 | 8/2004 | Clubb et al. | |
| 2004/0199199 A1 | 10/2004 | Krolik et al. | |
| 2005/0251198 A1 | 11/2005 | Smith et al. | |
| 2007/0073333 A1 | 3/2007 | Coyle | |

* cited by examiner

*Primary Examiner* — Elizabeth Houston
*Assistant Examiner* — Lindsey Bachman
(74) *Attorney, Agent, or Firm* — Seager, Tufte & Wickhem LLP (57) ABSTRACT

Embolic protection filtering devices and methods for making and using the same. An example embolic protection filter device may include an elongate shaft. A filter may be coupled to the shaft. The filter may include a filter frame and a filter membrane having a plurality of apertures formed therein attached to the filter frame. The filter may be configured to shift between a first collapsed configuration and a second expanded configuration. The apertures may have a first shape when the filter is in the first configuration and a second shape when the filter is in the second configuration.

5 Claims, 14 Drawing Sheets

EMBOLIC PROTECTION DEVICES WITH AN IMPROVED FILTER MEMBRANE

FIELD OF THE INVENTION

The present invention pertains to embolic protection filtering devices. More particularly, the present invention pertains to embolic protection filtering device with improved adhesion between the filter frame and the filter membrane.

BACKGROUND

Heart and vascular disease are major problems in the United States and throughout the world. Conditions such as atherosclerosis result in blood vessels becoming blocked or narrowed. This blockage can result in lack of oxygenation of the heart, which has significant consequences because the heart muscle must be well oxygenated in order to maintain its blood pumping action.

Occluded, stenotic, or narrowed blood vessels may be treated with a number of relatively non-invasive medical procedures including percutaneous transluminal angioplasty (PTA), percutaneous transluminal coronary angioplasty (PTCA), and atherectomy. Angioplasty techniques typically involve the use of a balloon catheter. The balloon catheter is advanced over a guidewire such that the balloon is positioned adjacent a stenotic lesion. The balloon is then inflated and the restriction of the vessel is opened. During an atherectomy procedure, the stenotic lesion may be mechanically cut away from the blood vessel wall using an atherectomy catheter.

During angioplasty and atherectomy procedures, embolic debris can be separated from the wall of the blood vessel. If this debris enters the circulatory system, it could block other vascular regions including the neural and pulmonary vasculature. During angioplasty procedures, stenotic debris may also break loose due to manipulation of the blood vessel. Because of this debris, a number of devices, termed embolic protection devices, have been developed to filter out this debris.

A wide variety of filtering devices have been developed for medical use, for example, intravascular use. Of the known filtering devices, each has certain advantages and disadvantages. There is an ongoing need to provide alternative filtering devices as well as alternative methods for manufacturing filtering devices.

BRIEF SUMMARY

The invention provides design, material, and manufacturing method alternatives for filtering devices. An example embolic protection filter device may include an elongate shaft. A filter may be coupled to the shaft. The filter may include a filter frame and a filter membrane having a plurality of apertures formed therein attached to the filter frame. The filter may be configured to shift between a first collapsed configuration and a second expanded configuration. The apertures may have a first shape when the filter is in the first configuration and a second shape when the filter is in the second configuration.

An example method for manufacturing an embolic protection device may include providing an elongate shaft, providing a filter frame, providing a filter membrane, forming a plurality of apertures having a first shape in the filter membrane, attaching the filter membrane to the filter frame, and attaching the filter frame to the shaft. The step of attaching the filter membrane to the filter frame may include stretching the filter membrane and shifting the apertures from the first shape to second expanded shape.

Another example embolic protection filter device may include an elongate shaft. A filter may be coupled to the shaft. The filter may include a filter frame and a filter membrane. A plurality of slits may be formed in the filter membrane. The filter may be configured to shift between a first collapsed configuration and a second expanded configuration. The slits may open when the filter is in the second configuration.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

DETAILED DESCRIPTION

The following description should be read with reference to the drawings wherein like reference numerals indicate like elements throughout the several views. The detailed description and drawings illustrate example embodiments of the claimed invention.

When a clinician performs an intravascular intervention such as angioplasty, atherectomy, and the like, embolic debris may dislodge from the blood vessel that can travel in the bloodstream to a position where it may impair blood flow, possibly leading to tissue damage. A number of other situations and/or interventions may also result in the mobilization of embolic debris. Accordingly, embolic protection filtering devices have been developed that can be disposed in the blood vessel downstream of the treatment site and expanded to capture debris.

Figure 1:
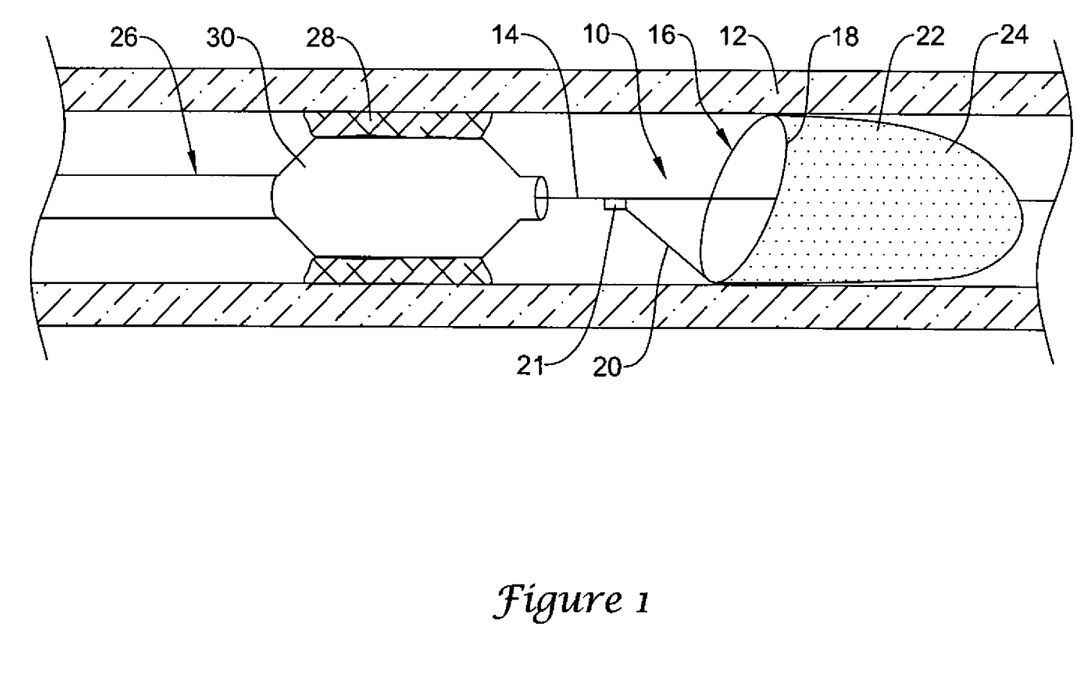
FIG. 1 is partial cross-sectional side view of an example filtering device disposed in a blood vessel.

FIG. 1 is a partial cross-sectional view of an example embolic protection filtering device 10 disposed within a blood vessel 12. Device 10 may include an elongate shaft or filter wire 14 having an embolic protection filter 16 coupled thereto. Filter 16 includes a filter frame 18 and a filter membrane or fabric 22 coupled to filter frame 18. Filter membrane 22 can be drilled (for example, formed by known laser techniques) or otherwise manufactured to include a plurality of openings 24. These holes or openings 24 can be sized to allow blood flow therethrough but restrict flow of debris or emboli floating in the body lumen or cavity.

In general, filter 16 may be adapted to operate between a first generally collapsed configuration and a second generally expanded configuration for collecting debris in a body lumen. To this end, in at least some embodiments, frame 18 may be comprised of a "self-expanding" shape-memory material such as nickel-titanium alloy, which is capable of biasing filter 16 toward being in the second expanded configuration. Additionally, filter frame 18 may include a radiopaque material or include, for example, a radiopaque wire disposed about a portion thereof. Some further details regarding these and other suitable materials are provided below.

One or more struts 20 may extend between filter frame 18 and filter wire 14. Strut 20 may be coupled to filter wire 14 by a coupling 21. Coupling 21 may be one or more windings of strut 20 about filter wire 14 or may be a fitting disposed over an end of strut 20 to attach it to filter wire 14. The exact arrangement of struts 20 can vary considerably. One of ordinary skill in the art would be familiar with the various arrangements of struts 20 that are appropriate for a given intervention.

With filter 16 properly positioned in blood vessel 12, another medical device may be advanced over filter wire 14 in order to treat and/or diagnose a lesion 28. For example, a catheter 26 (such as the balloon catheter depicted in FIG. 1) may be advanced over filter wire 14 in order to expand lesion 28. Of course numerous other devices could just as easily be passed over filter wire 14 including any device designed to pass through an opening or body lumen. For example, the device may comprise any type of catheter (e.g., therapeutic, diagnostic, or guide catheter), a stent delivery catheter, an endoscopic device, a laproscopic device, variations and refinements thereof, and the like, or any other suitable device. Alternatively, another device may be advanced over or through its own guiding structure to a suitable location adjacent filter 16 in a manner that allows device 10 to perform its intended filtering function.

Filtering device 10 is generally designed to filter embolic debris that might be generated during the course of this medical intervention. For example, device 10 can be used to capture embolic debris that might be generated during the use of catheter 26 such as when a balloon 30 (coupled to catheter 26) is inflated. It should be noted, however, that device 10 may find utility in concert with essentially any procedure that has the potential to loosen and release embolic debris in to the blood stream or with the devices associated with such procedures.

In addition to the features described above, device 10 may include a number of additional desirable features. For example, device 10 may be designed so as to have a reduced or otherwise "small" profile. Having a reduced profile may be desirable for a number of reasons. For example, reducing the profile of device 10 may allow device 10 cross lesion 28 while minimizing the chance of dislodging material at or adjacent lesion 28. Additionally, a reduced profile may allow device 10 to access deeper anatomy and/or vessels with a small diameter, including the neuroanatomy. The reduced profile of device 10 may be incorporated into device 10 in any one of a number of different ways. In at least some embodiments, reducing the profile of device 10 may be accomplished by utilizing less material for membrane 22. Because less material is utilized, membrane 22 may collapse down to a smaller size, for example, when filter 16 and/or frame 18 is collapsed (e.g., in the collapsed configuration).

Figure 2:
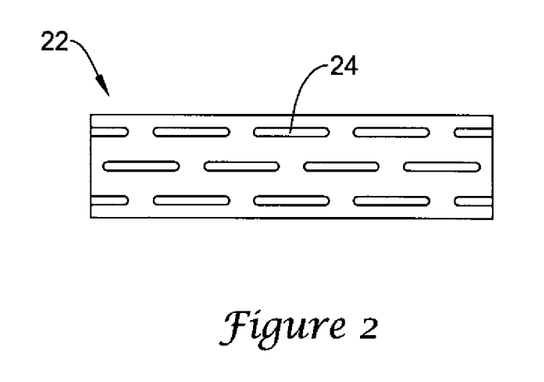
FIG. 2 is a side view of an example filter membrane.
Figure 3:
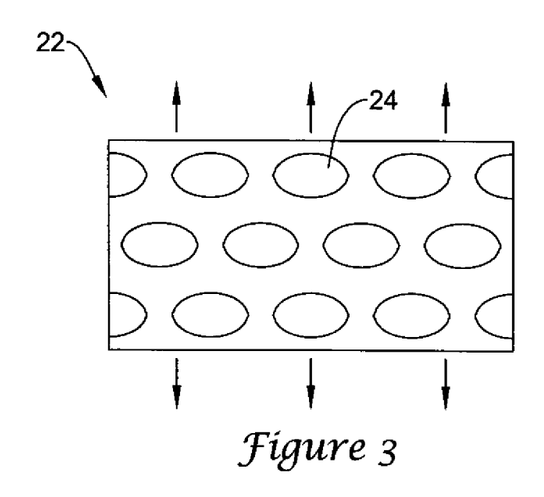
FIG. 3 is a side view of the filter membrane in FIG. 2 in an expanded configuration.

Several designs for membrane 22 that allow less material to be used are contemplated. At least some of these designs include the use of apertures 24 formed in membrane 22 that change shape when membrane 22 is expanded. This may include a change in shape (e.g., from a first shape to a second shape) that occurs when filter 16 is expanded, membrane 22 is expanded or stretched, and/or device 10 shifts to an expanded configuration. For example, FIG. 2 illustrates membrane 22 having apertures 24 that take the form of slots, slits, or slit-like openings. Such apertures 24 may generally have a shape that is longer in one direction (e.g., longitudinally) than in a direction normal to the first direction (e.g., radially). Other shapes and configurations are contemplated and some examples of the contemplated configurations are described below. When membrane 22 is expanded (e.g., when filter 16 is expanded), apertures change in shape as illustrated in FIG. 3. For example, apertures 24 may shift to a second shape that may be substantially round or otherwise more opened than the first shape. The changing of the shape of apertures may generally coincide with the expansion of filter 16 and/or device 10.

In general, apertures 24 are arranged in membrane 22 so that when membrane 22 is stretched or otherwise expanded, apertures 24 expand. Because apertures 24 can expand, a smaller "expandable" filter membrane 22 can be utilized in device 10. The smaller membrane 22, by virtue of it containing less material, may allow device 10 to be collapsed to a smaller profile.

Figure 4:
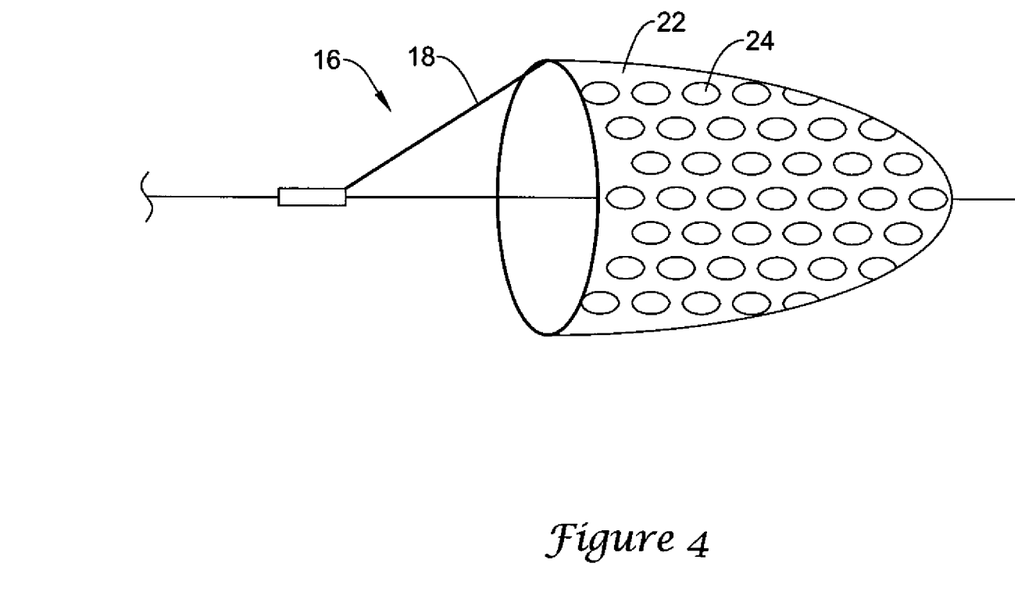
FIG. 4 is a side view of an example filter.
Figure 5:
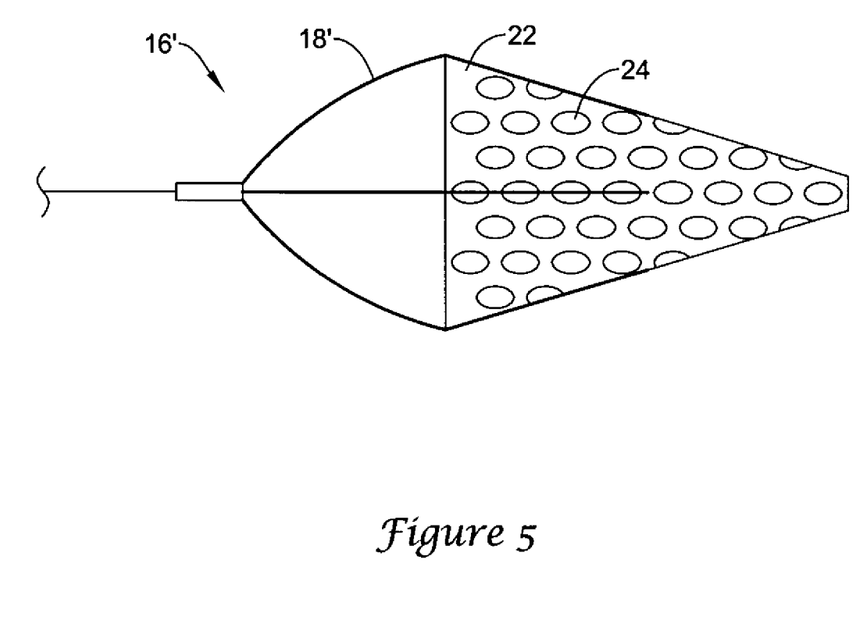
FIG. 5 is a side view of another example filter.

The shifting or changing in shape of apertures 24 may occur in a number of different types or forms of filter 16. For example, in at least some embodiments, filter 16 may include frame 18 that takes the form of a filter loop. This form is illustrated in FIG. 4. Thus, when frame 18 expands, membrane 22 may also expand and shift apertures 24 to a second shape. The same may be true when other forms of filter 16 are utilized as other embodiments of frame 18 are contemplated. For example, FIG. 5 illustrates filter 16' where frame 18' takes the form of an umbrella or umbrella-like frame. Thus, when frame 18' expands, membrane 22 may also expand and shift apertures 24 to a second shape. Of course, other frames are contemplated and shifting apertures 24 between the first and second shape may occur in an analogous manner in these frames.

Not only does utilizing membrane 22 having apertures that change in shape help to reduce the profile of device 10 (e.g., by reducing the amount of material needed for membrane 22), such a configuration may also provide additional desirable features to device 10. For example, the shifting of shapes for apertures 24 may be described as being a shift a first shape that may be collapsed or "closed" and a second shape that is expanded or "open". Thus, when apertures 24 are "open", they may be configured so that blood may flow through while embolic debris is captured. However, when apertures "close", apertures 24 may help to substantial hold or "seal" the captured embolic debris within membrane 22. This may help with the removal of the debris from the body and help to reduce the amount of debris that may be lost from membrane during the removal process. Furthermore, the extent to which apertures 24 open may be proportional to the extent to which membrane 22 is expanded. Thus, apertures 24 may be configured so that they open in a manner so as to allow blood flow therethrough that is proportional to the size of the vessel. This allows device 10 to be used in a number of differently sized vessels.

Figure 6:
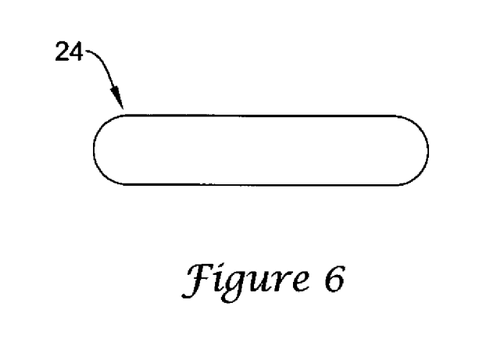
FIG. 6 is a side view of an example slit or aperture that may be formed in an example filter membrane.

In general, apertures 24 (and other apertures disclosed herein) may be formed in membrane 22 in any suitable manner. This may include mechanical cutting, laser cutting, chemical cutting, combinations thereof, and the like, or any other suitable method. The shape of apertures 24 can vary widely and include essentially any suitable shape including polygons, regular shapes, irregular shapes, random shapes, etc. FIGS. 6-15 illustrate some of the shapes contemplated for various apertures. For example, the slit-like or pill-shaped aperture 24 (which is illustrated in FIG. 2 as the first shape) is shown in FIG. 6. As shown in FIGS. 3-5, shifting aperture 24 to a second shape may include shifting aperture 24 to a substantially round shape. Other shapes may also be achieved depending on the size, shape, and configuration of membrane 22. For example, some embodiments of membrane 22 may be configured so that aperture 24 has a second shape other than substantially round.

Figure 7:
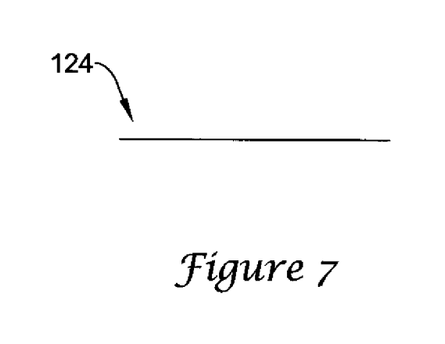
FIG. 7 is a side view of another example aperture that may be formed in a filter membrane.

FIG. 7 illustrates aperture 124 that resembles a slit or thin slit. Apertures 124 may be formed in membrane 22 by making a small cut in membrane 22, but without any substantially removal of material. These apertures may similarly expand to an oval or substantially round shape.

Figure 8:
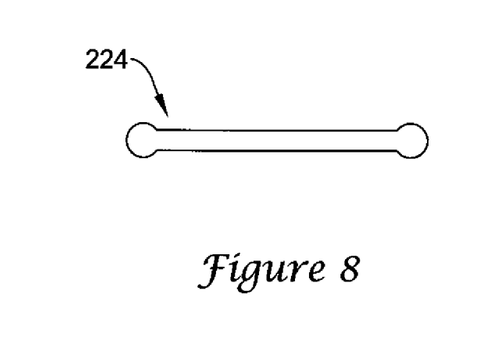
FIG. 8 is a side view of another example aperture that may be formed in a filter membrane.
Figure 9:
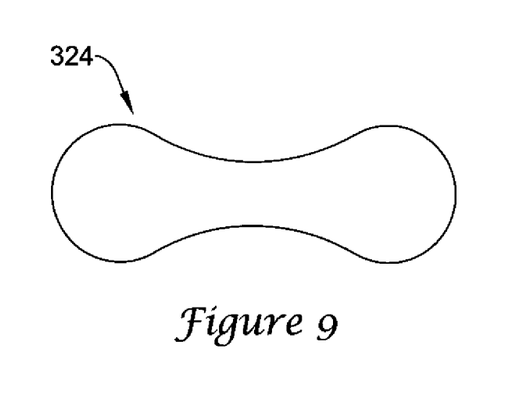
FIG. 9 is a side view of another example aperture that may be formed in a filter membrane.
Figure 10:
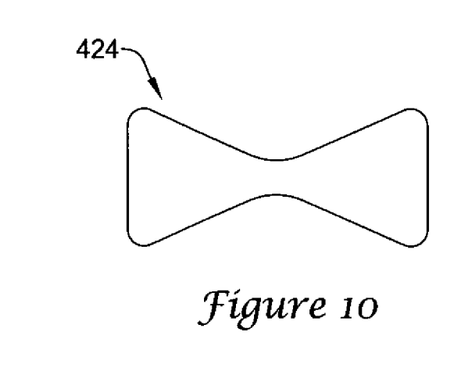
FIG. 10 is a side view of another example aperture that may be formed in a filter membrane.
Figure 11:
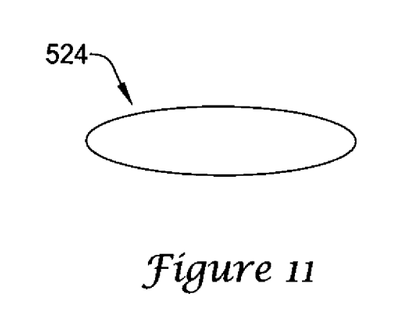
FIG. 11 is a side view of another example aperture that may be formed in a filter membrane.
Figure 12:
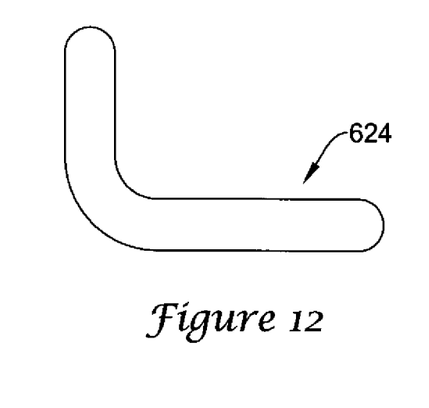
FIG. 12 is a side view of another example aperture that may be formed in a filter membrane.
Figure 13:
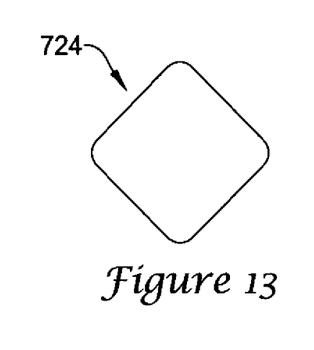
FIG. 13 is a side view of another example aperture that may be formed in a filter membrane.
Figure 14:
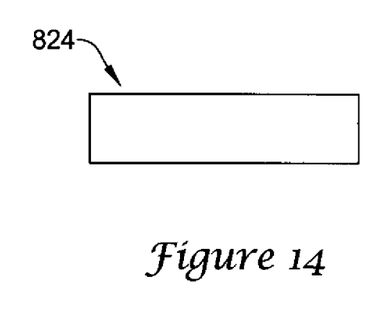
FIG. 14 is a side view of another example aperture that may be formed in a filter membrane.
Figure 15:
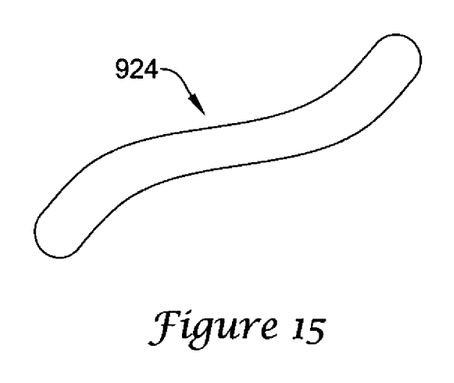
FIG. 15 is a side view of another example aperture that may be formed in a filter membrane.

FIGS. 8-15 illustrate some additional shapes for apertures. The shapes illustrated may represent the first or collapsed shape or the second or expanded shape in any one of a number of different embodiments of apertures. FIG. 8 illustrates aperture 224 having a thin dumb-bell shape. FIG. 9 illustrates aperture 324 having an enlarged dumb-bell shape. FIG. 10 illustrates aperture 424 having an hourglass shape. FIG. 11 illustrates aperture 524 having an elliptical or oval shape. FIG. 12 illustrates aperture 624 having an "L" shape or otherwise including a bend or arc. FIG. 13 illustrates aperture 724 having a diamond shape. FIG. 14 illustrates aperture 824 having a rectangular shape. FIG. 15 illustrates aperture 924 having a curved or wavy shape.

In some embodiments, the apertures may be arranged to provide auxetic properties to filter membrane 22. Thus, membrane 22 may be understood to be an auxetic material. Auxetic materials may be understood as being materials that become wider or thicker perpendicularly to the direction of the applied force when stretched. For example, when a square aperture (not shown but contemplated) is stretched, it may be wider or thicker perpendicularly to the direction of the applied force. This may result in an aperture that resembles aperture 424 (illustrated in FIG. 10). Other apertures may also be analogously arranged to provide auxetic properties to filter membrane 22.

In various embodiments of device 10, any shape of apertures may be utilized including any of those disclosed herein. In some embodiments, all of the apertures may have the same shape (e.g., the same first shape). However, other embodiments are contemplated where a first aperture 24 (or group of apertures) has one shape and another aperture 24 (or group of apertures 24) has a different shape. Thus, numerous devices are contemplated that utilize only one aperture shape or that utilize two, three, four, five, six, or more differently shaped apertures including any of those aperture shapes disclosed herein.

Figure 16:
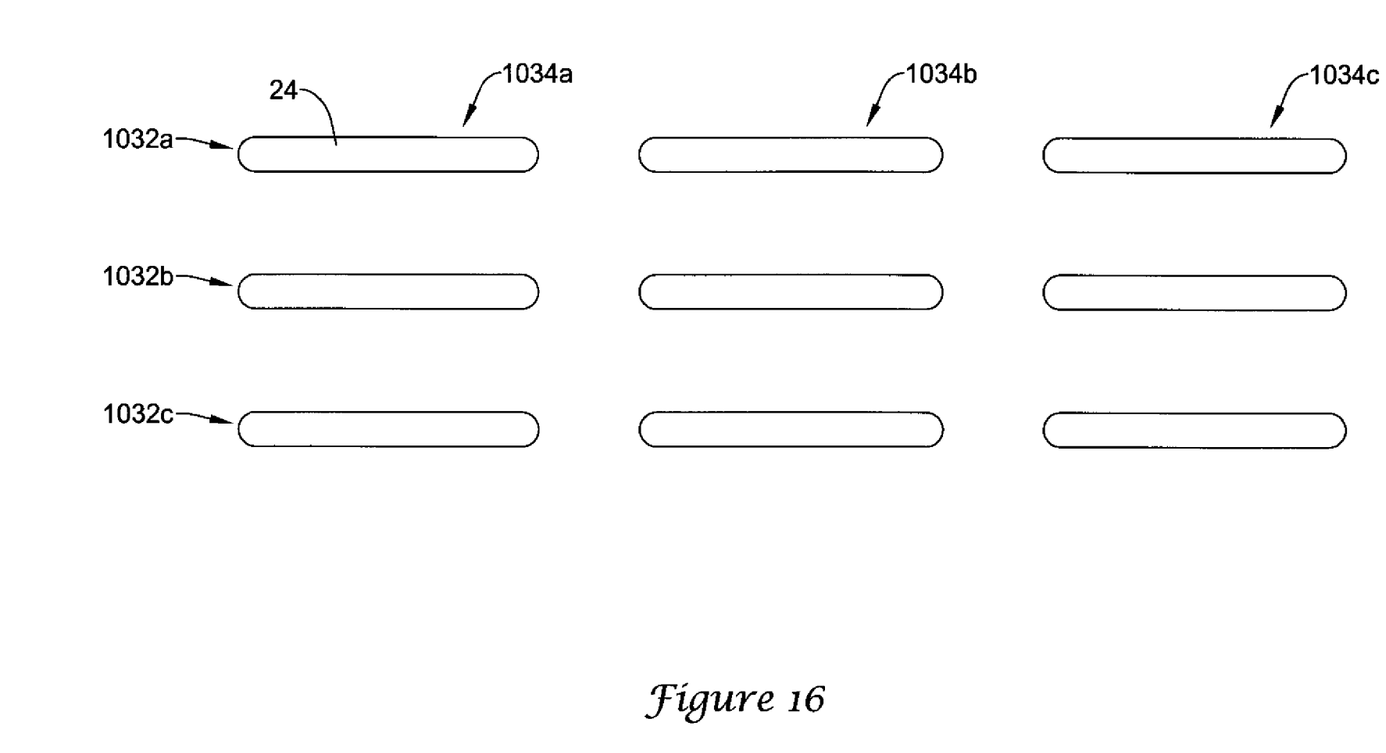
FIG. 16 is a side view of an example pattern or configuration of apertures that may be utilized in a filter membrane.
Figure 17:
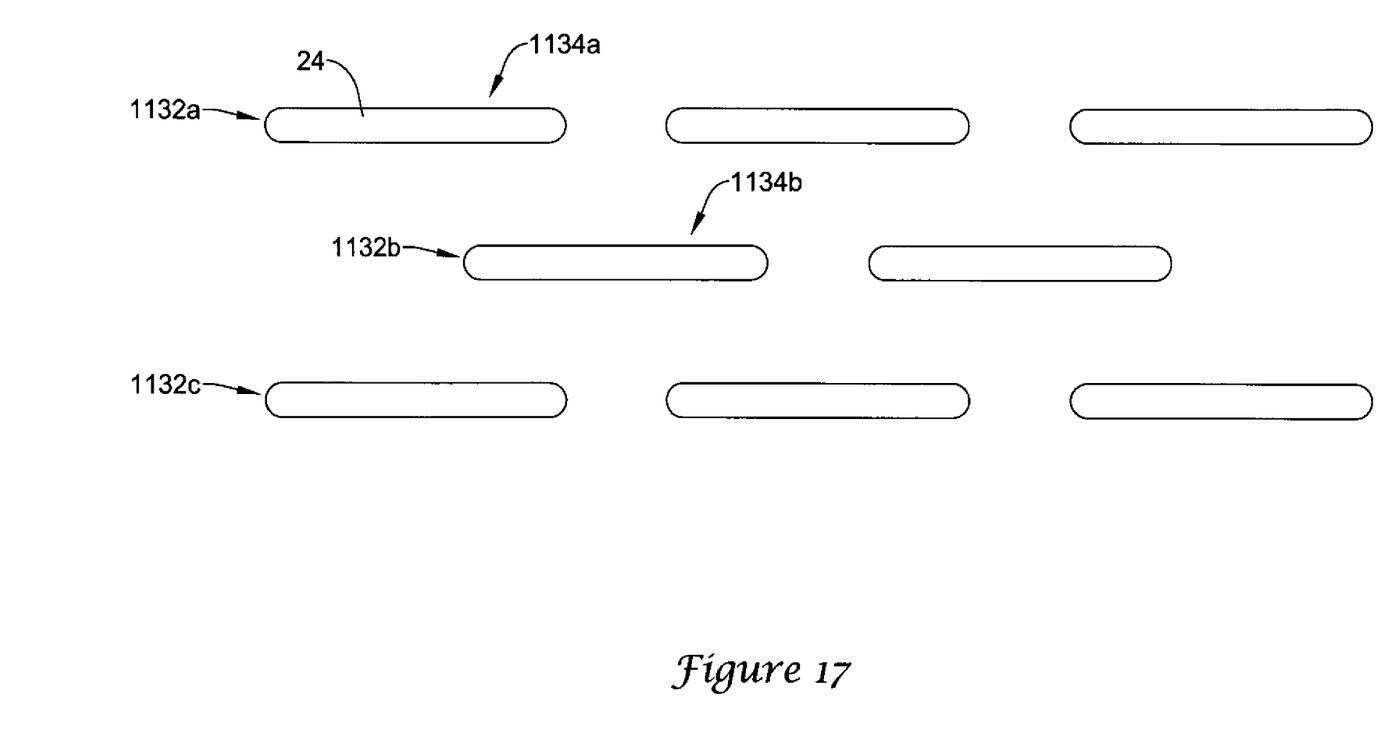
FIG. 17 is a side view of another example pattern or configuration of apertures that may be utilized in a filter membrane.

The apertures utilized in any given membrane 22 can be arranged in any suitable pattern along membrane 22. FIGS. 16-20 illustrate some of the patterns contemplated for example apertures 24. For example, FIG. 16 illustrates that apertures 24 may be arranged in a series of longitudinally-aligned rows 1032a/1032b/1032c. These rows may be radially-aligned in a series of columns 1034a/1034b/1036c. Such a pattern may be described as a "regular" or aligned pattern. FIG. 17 illustrates another example pattern where apertures are arranged in a series of longitudinally-aligned rows 1132a/1132b/1132b and a series of radially offset columns 1134a/1134b. Such a pattern may be described as an "offset" pattern where apertures 24 are offset with respect to one another.

Figure 18:
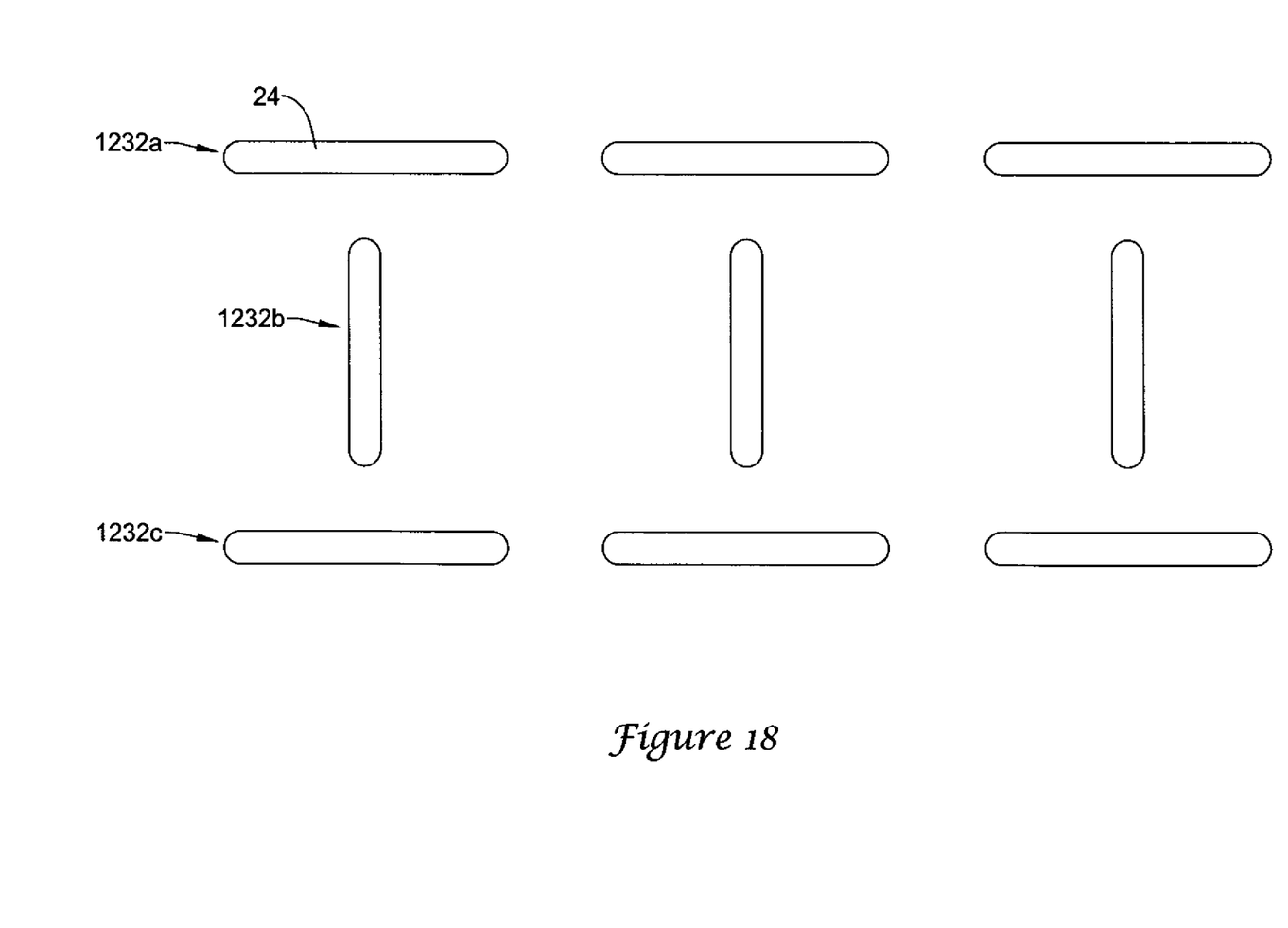
FIG. 18 is a side view of another example pattern or configuration of apertures that may be utilized in a filter membrane.

FIG. 18 illustrates another example pattern where apertures 24 are arranged in a series of longitudinally-aligned rows 1232a/1232b/1232c. However, the rows 1232a/1232b/1232c alternate between an arrangement where apertures 24 have a substantially horizontal orientation (e.g., rows 1232a/1232c) and rows where apertures 24 have a substantially vertical orientation (e.g., row 1232b). Such a pattern may be described as an "alternating" pattern.

Figure 19:
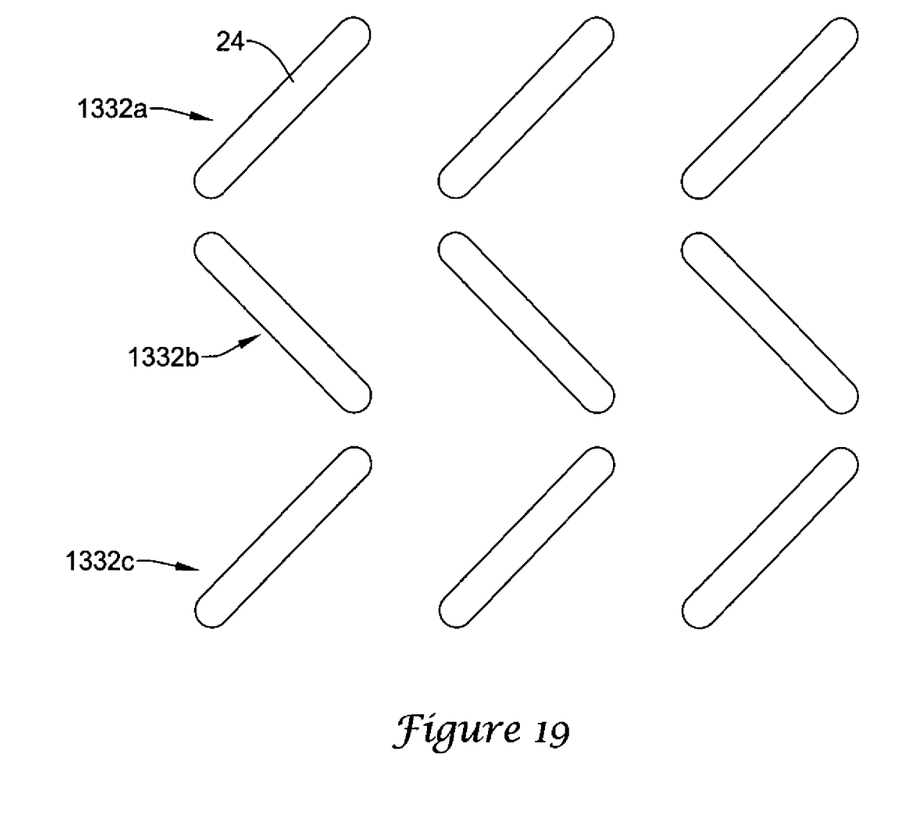
FIG. 19 is a side view of another example pattern or configuration of apertures that may be utilized in a filter membrane.

FIG. 19 illustrates another example pattern where apertures 24 are arranged in a series of longitudinally-aligned rows 1332a/1332b/1332c. Within these rows, apertures 24 have a diagonal orientation. However, the direction of the apertures changes. For example, in some of the rows, apertures 24 are oriented in one direction (e.g., rows 1332a/1332c) while in other rows apertures 24 are oriented in the opposite direction (e.g., row 1332b). Such a pattern may be described as an "alternating diagonal" pattern.

Figure 20:
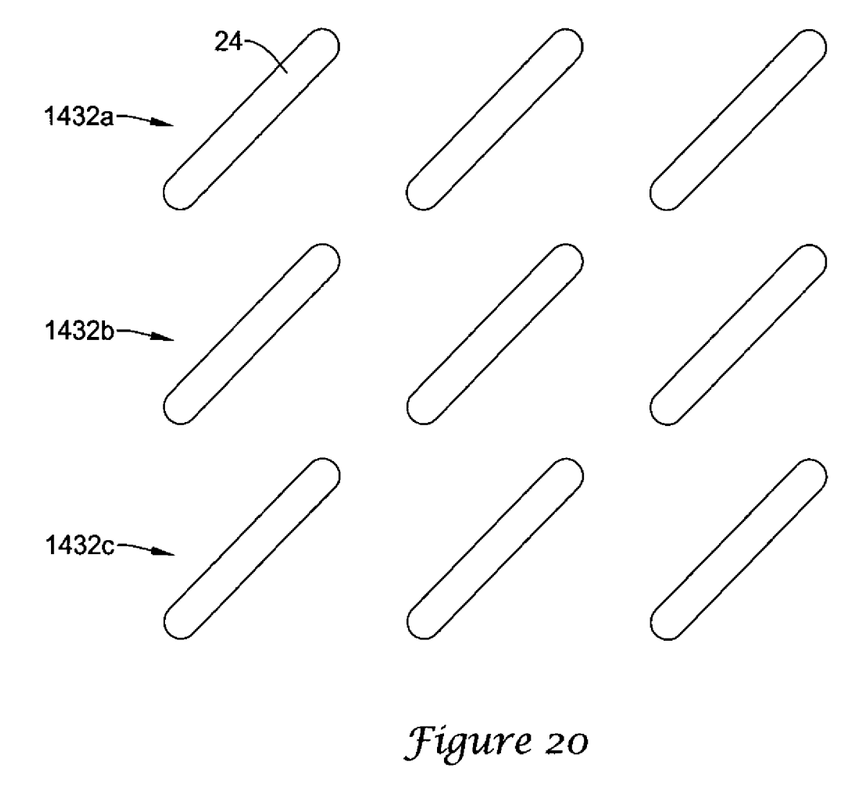
FIG. 20 is a side view of another example pattern or configuration of apertures that may be utilized in a filter membrane.

FIG. 20 illustrates another example pattern where apertures 24 are arranged in a series of longitudinally-aligned rows 1432a/1432b/1432c. Within these rows, apertures 24 have a diagonal orientation. In this example, all of the rows 1432a/1432b/1432c have apertures 24 that are oriented in the same direction. Such a pattern may be described as an "aligned diagonal" pattern.

Any of the patterns shown herein may be utilized for apertures 24 in any suitable membrane 22. Additionally, any suitable combination of patterns may also be used. Numerous other patterns are contemplated including any suitable regular, irregular, random, or other type of pattern.

Figure 21:
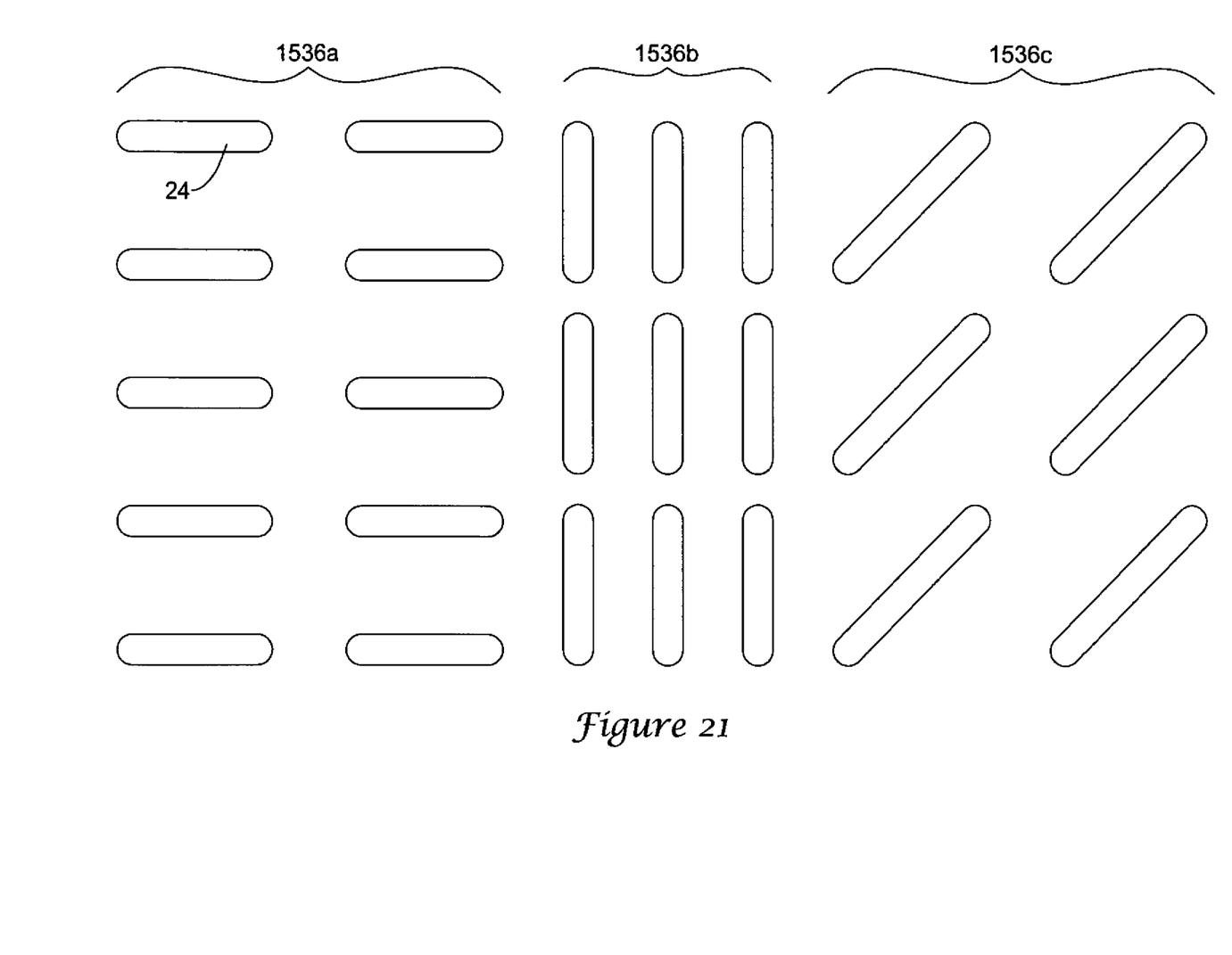
FIG. 21 is a side view of another example pattern or configuration of apertures that may be utilized in a filter membrane.
Figure 22:
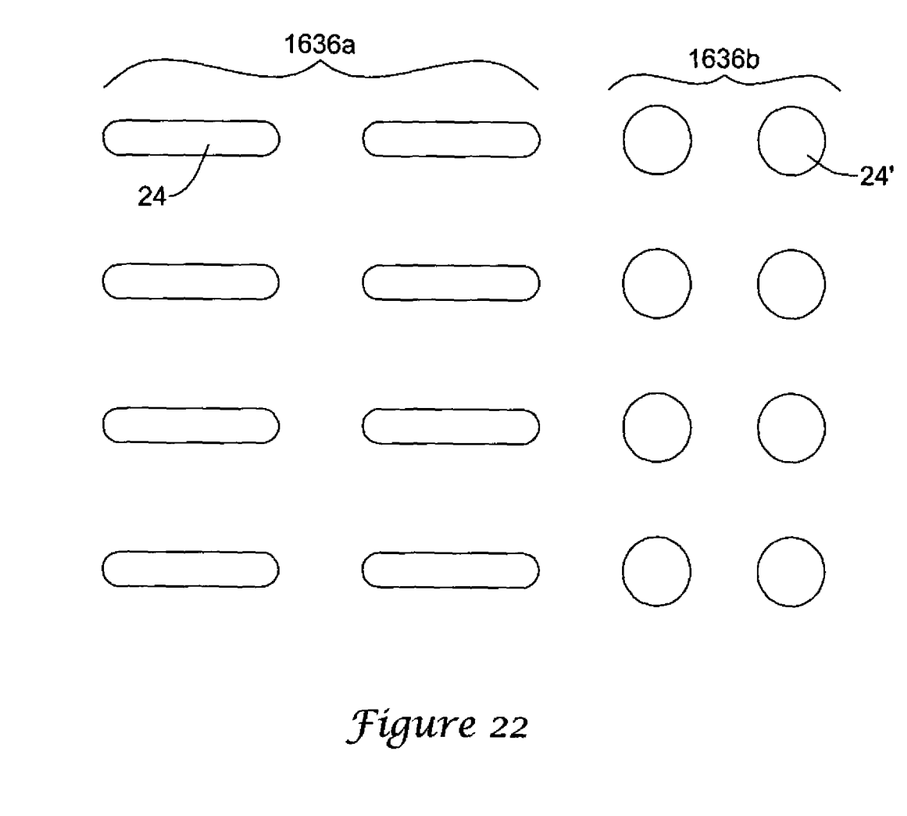
FIG. 22 is a side view of another example pattern or configuration of apertures that may be utilized in a filter membrane.

FIG. 21-22 illustrates additional example patterns of apertures 24 where groups of apertures are defined that differ in configuration. For example, in FIG. 21 apertures 24 are arranged so as to define a first group 1536a of horizontally-oriented apertures 24. Apertures 24 are also arranged so as to define a second group 1536b of vertically-oriented apertures 24 and a third group 1536c of diagonally-oriented apertures 24. This figure illustrates that a plurality of different patterns may be utilized in a variety of different contemplated membranes 22.

In FIG. 22, different groupings of apertures are utilized that bear different types or shapes of apertures 24. For example, group 1636a includes slot-like apertures 24 whereas group 1636b includes substantially round apertures 24'. Apertures 24' may resemble the openings found in typical embolic protection filter membranes. This figure illustrates that many membranes 22 are contemplated that may include two or more different types or shapes of apertures and that these different types of apertures may arranged in any suitable pattern.

The method for manufacturing device 10 may include a variety of steps. For example, the method may include provide a shaft such as wire 14, providing frame 18 (or 18'), providing membrane 22, forming a plurality of apertures 24 in membrane 22, attaching membrane 22 to frame 18, and attaching frame 18 to shaft 14. The step of attaching membrane 22 to frame 18 may include stretching filter membrane 22 and shifting apertures 24 from the first shape to second expanded shape. However, apertures 24 may shift back to the first shape when device 10 is collapsed. Thus, apertures 24 can shift between the first shape and the second shape.

The materials that can be used for the various components of device 10 (and/or other devices disclosed herein) may include those commonly associated with medical devices. For simplicity purposes, the following discussion makes reference to frame 18 and other components of device 10. However, this is not intended to limit the invention as the discussion may be applied to other similar frames and/or components of filters, frames, or devices disclosed herein.

Frame 18 may be made from a metal, metal alloy, polymer (some examples of which are disclosed below), a metal-polymer composite, combinations thereof, and the like, or any other suitable material. Some examples of suitable metals and metal alloys include stainless steel, such as 304V, 304L, and 316LV stainless steel; mild steel; nickel—titanium alloy such as linear-elastic and/or super-elastic nitinol; other nickel alloys such as nickel—chromium—molybdenum alloys (e.g., UNS: N06625 such as INCONEL® 625, UNS: N06022 such as HASTELLOY® C-22®, UNS: N10276 such as HASTELLOY®C276®, other HASTELLOY® alloys, and the like), nickel—copper alloys (e.g., UNS: N04400 such as MONEL® 400, NICKELVAC® 400, NICORROS® 400, and the like), nickel—cobalt—chromium—molybdenum alloys (e.g., UNS: R30035 such as MP35-N® and the like), nickel—molybdenum alloys (e.g., UNS: N10665 such as HASTELLOY® ALLOY B2®), other nickel—chromium alloys, other nickel—molybdenum alloys, other nickel—cobalt alloys, other nickel—iron alloys, other nickel—copper alloys, other nickel—tungsten or tungsten alloys, and the like; cobalt—chromium alloys; cobalt—chromium—molybdenum alloys (e.g., UNS: R30003 such as ELGILOY®, PHYNOX®, and the like); platinum enriched stainless steel; titanium; combinations thereof; and the like; or any other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. These materials may be appropriate for frame 18, membrane 22, and/or other components of device 10.

As alluded to above, within the family of commercially available nickel—titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2-0.44% strain before plastically deforming.

In some embodiments, the linear elastic and/or non-super-elastic nickel-titanium alloy is an alloy that does not show any martensite/austenite phase changes that are detectable by DSC and DMTA analysis over a large temperature range. For example, in some embodiments, there may be no martensite/austenite phase changes detectable by DSC and DMTA analysis in the range of about −60° C. to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties and has essentially no yield point.

In some embodiments, the linear elastic and/or non-super-elastic nickel—titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of frame 18 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of device 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of device 10 to achieve the same result.

In some embodiments, a degree of MRI compatibility is imparted into device 10. For example, to enhance compatibility with Magnetic Resonance Imaging (MRI) machines, it may be desirable to make core wire 18 and/or tubular member 20, or other portions of frame 18 that would impart a degree of MRI compatibility. For example, frame 18 may be made of a material that does not substantially distort the image and create substantial artifacts (artifacts are gaps in the image). Certain ferromagnetic materials, for example, may not be suitable because they may create artifacts in an MRI image. Frame 18 may also be made from a material that the MRI machine can image. Some materials that exhibit these characteristics include, for example, tungsten, cobalt—chromium—molybdenum alloys (e.g., UNS: R30003 such as ELGILOY®, PHYNOX®, and the like), nickel—cobalt—chromium—molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. An embolic protection filter device, comprising:
an elongate shaft;
a filter coupled to the shaft, the filter including a filter frame and a filter membrane;
wherein a plurality of slits are formed in the filter membrane without any substantial removal of material;
wherein the filter is configured to shift between a first collapsed configuration and a second expanded configuration; and
wherein the slits open when the filter is in the second configuration.

2. The filter device of claim 1, wherein the apertures are arranged in longitudinally-aligned rows or radially-aligned columns.

3. The filter device of claim 1, wherein at least some of apertures are offset with respect to one another.

4. The filter device of claim 1, wherein the filter frame includes an umbrella-like frame.

5. The filter device of claim 1, wherein the filter frame includes a filter loop.

* * * * *